(12) United States Patent
Janssen et al.

(10) Patent No.: US 9,175,378 B2
(45) Date of Patent: Nov. 3, 2015

(54) METHOD FOR IMPROVING THE WEAR RESISTANCE OF DYED SURGICAL INSTRUMENTS

(75) Inventors: Albert Peter Gerhard Janssen, Chur (CH); Gabriella Sinicco, Pfäffikon SZ (CH)

(73) Assignee: OERLIKON SURFACE SOLUTIONS AG, TRUBBACH, Trubbach (CH)

( * ) Notice: Subject to any disclaimer, the term of this patent is extended or adjusted under 35 U.S.C. 154(b) by 0 days.

(21) Appl. No.: 14/232,393

(22) PCT Filed: Jul. 10, 2012

(86) PCT No.: PCT/EP2012/002910
§ 371 (c)(1),
(2), (4) Date: Feb. 17, 2014

(87) PCT Pub. No.: WO2013/010647
PCT Pub. Date: Jan. 24, 2013

(65) Prior Publication Data
US 2014/0171924 A1 Jun. 19, 2014

(30) Foreign Application Priority Data
Jul. 15, 2011 (DE) .......................... 10 2011 107 787

(51) Int. Cl.
| | |
|---|---|
| C23C 14/06 | (2006.01) |
| C23C 14/02 | (2006.01) |
| C23C 14/00 | (2006.01) |
| C23C 14/08 | (2006.01) |
| C23C 14/58 | (2006.01) |
| A61L 31/02 | (2006.01) |
| A61L 31/08 | (2006.01) |

(52) U.S. Cl.
CPC ........... *C23C 14/0641* (2013.01); *A61L 31/022* (2013.01); *A61L 31/088* (2013.01); *C23C 14/0015* (2013.01); *C23C 14/025* (2013.01); *C23C 14/083* (2013.01); *C23C 14/5853* (2013.01)

(58) Field of Classification Search
CPC .... C23C 14/08; C23C 14/024; C23C 14/027; C23C 14/0641
USPC ................................. 427/2.1, 419.2
See application file for complete search history.

(56) References Cited

U.S. PATENT DOCUMENTS

| | | | | |
|---|---|---|---|---|
| 4,981,756 | A * | 1/1991 | Rhandhawa | 428/336 |
| 6,988,318 | B2 * | 1/2006 | Buchtmann et al. | 30/350 |
| 7,673,541 | B2 * | 3/2010 | Skrobis et al. | 76/104.1 |
| 2008/0178477 | A1 * | 7/2008 | Buchtmann | 30/350 |
| 2010/0098911 | A1 * | 4/2010 | Tanibuchi et al. | 428/141 |
| 2010/0255337 | A1 | 10/2010 | Langhorn | |

FOREIGN PATENT DOCUMENTS

| | | |
|---|---|---|
| DE | 19809932 C1 * | 10/1999 |
| EP | 0608997 A1 | 8/1994 |
| EP | 1652963 A1 | 5/2006 |

OTHER PUBLICATIONS

International Search Report for Application No. PCT/EP2012/002910 dated Oct. 26, 2012.
Geetha M. et al. "Ti based biomaterials, the ultimate choice for orthopaedic implants—A review". Progress in Materials Science, Pergamon Press GB. vol. 54, No. 3 dated May 1, 2009.

* cited by examiner

*Primary Examiner* — Cachet Sellman
(74) *Attorney, Agent, or Firm* — Pearne & Gordon LLP

(57) ABSTRACT

The present invention relates to a method for improving the wear resistance of dyed surgical instruments having a vacuum-resistant material as the main body which, over the course of a vacuum coating step, is coated with a thin layer of titanium, and the coated surface is subjected to anodic oxidation. The method is characterized in that, over the course of the vacuum coating step, prior to coating with the layer of titanium, at least parts of the main body are coated with a layer of hard material which improves the wear protection.

21 Claims, No Drawings

METHOD FOR IMPROVING THE WEAR RESISTANCE OF DYED SURGICAL INSTRUMENTS

FIELD OF THE INVENTION

The present invention relates to a method for improving the wear resistance of surgical instruments that have been or are to be dyed.

DESCRIPTION OF RELATED ART

Dyed surgical instruments are very common. The dyeing enables for example a clear distinction to be made between an instrument and an implant. But it is also easier to distinguish better between different instruments if these have a different color. The main purpose of the dyeing, which as a general rule is achieved by color anodizing, is the identification of implants before and during the surgical operation (colored size marking). The applications include among others both dental as well as orthopedic implants as well as osteosynthesis products such as screws, plates or instruments. One side effect of dyeing is also to inhibit the release of aluminum and vanadium ions from the titanium alloy.

DE19809932 discloses a method for dyeing surgical instruments consisting of a vacuum resistant and high-temperature proof plastic or of steel. The instruments are accordingly coated with a thin titanium coating with a thickness between 2 μm and 10 μm in a vacuum facility of a known type. Subsequently, this coating is oxidized by anodic oxidation on its surface in a layer thickness in the nanometer range. For this, the instrument is held in an electrolyte, that contains for example 1.7% citric acid, and the part to be oxidized is connected as anode. The document describes that a titanium sheet can serve as cathode. In DE19809932, a DC voltage of maximum 130 Volt is applied to the electrodes, wherein the level of the voltage has an influence on the color that can be achieved. The titanium coating is then anodized on the surface with a current density on the order of between 100 and 200 mA, with a layer thickness on the order of 50 nm to 250 nm.

However, the above surgical instruments have not so far been protected against wear and tear, since the organic materials that are to be treated with the instruments are mostly soft and implants are usually given their final form already during manufacture. However, after a short period of time dyed surgical instruments according to the state of the art already exhibit patch-like color changes that cause doubts to arise as regards their use at least for the patient.

BRIEF SUMMARY OF THE INVENTION

The aim of the invention is therefore to propose a method with which the occurrence of wear and tear described above can be avoided or at least temporarily delayed.

According to the invention, this aim is achieved with the method according to claim 1 and with a surgical instrument according to claim 9. The dependent claims describe different and preferred embodiments.

To their surprise, the inventors were able to discover that the apparition of spots were in fact wear and tear phenomena. It is probable that during the hectic everyday life of surgery, instruments more often than previously suspected get hit for example on containers out of which they are removed or into which they are placed. It can sometimes also happen that such an instrument gets dropped and that the fall subjects it to a considerable shock.

If the substrate bearing a titanium oxide layer does not afford this titanium oxide layer sufficient stability, it can collapse and the spots described above can occur. A thin titanium layer as described in DE19809932 in particular is not capable of providing sufficient stability to the titanium oxide layer generated by anodizing. By contrast, the measures of the present invention have a stabilizing effect. In fact, by providing a layer of hard material between the main body and the titanium oxide coating, the substrate of the titanium oxide layer is imparted sufficient stability to give enough support for the titanium oxide coating.

In case a metallic titanium layer is provided under the titanium oxide layer, for example in order for a titanium oxide coating to be generated through anodic oxidation, the layer of hard material between the substrate and the metallic titanium coating is provided. This metallic titanium layer should however be a thin layer.

A layer is "thin" in the sense of the present invention if its thickness does not exceed 20 μm. In the case of titanium layer thicknesses greater than 20 μm, the relatively low hardness of titanium has a negative effect, so that the stabilizing bonding layer for the titanium oxide layer loses its effect.

Some medical applications however exclude the use of metallic titanium coatings. To generate the titanium oxide coating, the application of anodic oxidation is not an option. There is however the possibility of achieving such a titanium oxide layer directly by means of a vacuum coating method, in particular through a PVD process. The PVD process known as reactive sputtering, where material is knocked off from a titanium target by means of ion bombardment in a reaction with reactive gas, is particularly suited. In the present case, the reactive gas includes oxygen, so that the desired titanium oxide layer is formed on the substrate to be coated. The advantage of such a method lies among others in that it is not necessary to provide a metallic titanium layer between the substrate and the oxide layer.

Even if a metallic titanium layer is desired, the sputtering process can advantageously be used for generating the titanium oxide layer since it is readily possible to operate the sputtering process first without reactive gas, so that first a metallic titanium layer is deposited onto the substrate.

DETAILED DESCRIPTION OF THE INVENTION

The following description of a preferred embodiment serves to explain the invention in more detail. By way of example, a surgical forceps treated according to the invention will be described. In this respect, it is advantageous to first clean the surface of the forceps body since the layer-to-substrate boundary surface should be as free from contaminations as possible in order to ensure adhesion. If for example steel is used, a chromium oxide layer is often formed on the steel surface that should be removed prior to the vacuum coating. This can be done with suitable methods, such as for example CD or RF sputter cleaning in argon-hydrogen plasma. The surgical forceps is then coated in a vacuum coating facility by means of coating from the gaseous phase (PVD=physical vapor deposition), first with a 0.5 μm thick chromium layer as bonding layer. In the same coating facility and without breaking the vacuum, a 3 μm thick chromium nitride layer is subsequently applied by means of sputtering from a chromium magnetron target and while nitrogen is let into the chamber as a reactive gas. Then, in the same coating facility and without breaking the vacuum, sputtering takes place from a titanium target and a 5 μm thick titanium layer is accordingly deposited.

The forceps thus coated is then subjected to anodic oxidation similarly to the method described above in relation to DE19809932. Oxide layer thicknesses of between 10 nm and 250 nm are useful. The forceps has the color desired by the user. Due to the layer of hard material lying under the titanium layer, the color also remains locally when subjected to shocks as they occur in everyday life of surgery.

According to a second embodiment, instead of the chromium nitride layer a titanium nitride layer is deposited by means of arc evaporation. It is then possible during the coating process to vary the nitrogen supply continuously and/or incrementally, and in particular to reduce it, thus generating a gradient layer at the end of which no nitrogen is present anymore. In this manner, a good transition to the titanium layer is formed.

It is also possible by using CrN to achieve a gradient and thus a transition to the titanium. For this, however, it is as a general rule necessary to have two targets run in parallel (Cr and Ti) and to reduce the sputtering output of the Cr in parallel to the nitrogen flow. Although this is feasible, it is technically somewhat more difficult.

According to a further embodiment of the present invention, a chromium bonding layer and a chromium nitride layer of hard material are deposited onto the forceps body, as described above. Subsequently, sputtering takes place from a titanium target and a titanium oxide layer is deposited onto the forceps body under adjunction of reactive gas, which comprises oxygen and preferably essentially consists of oxygen.

It must be noted that in case the substrate material has a sufficiently high intrinsic hardness and the titanium oxide bonds onto the substrate in a sufficient manner, if may be possible to do without the layer of hard material.

A method has been disclosed for improving the wear resistance of dyed surgical instruments having a vacuum-resistant material as the main body which, over the course of a vacuum coating step is coated with a thin titanium layer, and the coated surface is subjected to anodic oxidation. Alternatively, it is possible to produce the titanium oxide layer by means of reactive deposition from the vapor phase in a vacuum coating facility, so that it is possible to do without the anodic oxidation and possibly also without the titanium layer. The method is characterized in that, over the course of the vacuum coating step, prior to coating with the layer of titanium, at least parts of the main body are coated with a layer of hard material which improves protection against wear and tear.

The layer of hard material can be formed by means of a nitride and/or oxide of at least one metal and/or of at least one alloy.

The nitride and/or oxide can be formed with titanium and/or chromium.

The layer of hard material can be formed by means of a chromium nitride layer, preferably by means of magnetron sputtering.

The layer of hard material can be formed by means of a titanium nitride layer, preferably by means of arc evaporation.

The layer of hard material can be deposited with a thickness of at least 1.5 µm and maximum 20 µm and is preferably deposited between 2 µm and 5 µm.

The titanium layer is deposited with a thickness of at least 1 µm, preferably between 2 µm and 10 µm and preferably directly onto the layer of hard material.

To improve the adhesion of the layer of hard material onto the main body, a bonding layer, preferably of chromium, may be provided between the main body and the layer of hard material.

A surgical instrument with a main boy and a titanium coating has been disclosed, whose outermost layer comprises an oxide layer, wherein a layer of hard material may be provided between the main body and the layer of hard material.

The layer of hard material can preferably have a thickness between 2 µm and 10 µm and comprise titanium nitride and/or chromium nitride.

Between the main body and the layer of hard material, a bonding layer, preferably a chromium layer, may be provided.

The present invention has been described by way of example on the basis of a coloring titanium oxide layer. Although such a layer is to be preferred, similar results can however be achieved with zirconium oxide (e.g. ZrO) and/or niobium oxide (e.g. $Nb_2O$). Furthermore, it is possible to form an alternating layer system (with titanium oxide and/or zirconium oxide and/or niobium oxide), which on the basis of interference effects of the layers can result in particular color effects.

What is claimed is:

1. Method for improving the wear resistance of dyed surgical instruments having a vacuum-resistant material as a main body which is coated with a titanium layer, characterized in that, over the course of a vacuum coating step, prior to coating with the layer of titanium, at least parts of the main body are coated with a layer of hard material which improves the wear protection.

2. Method according to claim 1, characterized in that production of a titanium oxide layer on the main body comprises a vapor deposition from a vapor phase in a vacuum coating facility, wherein in the course of the deposition either the titanium oxide layer is deposited on the main body by means of sputtered or vaporized titanium with the aid of oxygen as reactive gas or in the course of the vapor deposition the titanium layer is deposited on the main body and subjected to anodic oxidation to convert the titanium layer to the titanium oxide layer.

3. Method according to claim 2, characterized in that the nitride and/or oxide is formed with titanium and/or chromium.

4. Method according to claim 1, characterized in that the layer of hard material is formed by means of a nitride and/or oxide of at least one metal and/or of at least one alloy.

5. Method according to claim 1, characterized in that the layer of hard material can be formed by means of a chromium nitride layer.

6. Method according to claim 1, characterized in that the layer of hard material is formed by means of a titanium nitride layer.

7. Method according to claim 1, characterized in that the layer of hard material is deposited with a thickness of at least 1.5 µm and maximum 20 µm.

8. Method according to claim 1, characterized in that in the case of a deposited titanium layer, the layer is deposited with a thickness of at least 1 µm.

9. Method according to claim 1, characterized in that to improve the adhesion of the layer of hard material onto the main body, a bonding layer is provided between the main body and the layer of hard material.

10. Method according to claim 1, characterized in that the layer of hard material is deposited as a gradient layer and thus a gradual transition to a titanium oxide layer or to the titanium layer is achieved.

11. Method according to claim 1, characterized in that the layer of hard material is deposited with a thickness of at least 2 µm and a maximum of 5 µm.

12. Method according to claim 1, characterized in that in the case of a deposited titanium layer, the layer is deposited with a thickness of at least 2 μm and a maximum of 10 μm.

13. Method according to claim 1, characterized in that in the case of a deposited titanium layer, the layer is deposited with a thickness of at least 2 μm and a maximum of 10 μm directly onto the layer of hard material.

14. Method according to claim 1, characterized in that to improve the adhesion of the layer of hard material onto the main body, a bonding layer of chromium is provided between the main body and the layer of hard material.

15. Method according to claim 1, characterized in that production of a titanium oxide layer on the main body comprises a vapor deposition from a vapor phase in a vacuum coating facility, wherein in the course of the vapor deposition the titanium oxide layer is formed by depositing titanium oxide on the main body by means of sputtered or vaporized titanium with the aid of oxygen as reactive gas.

16. Surgical instrument with a main body and a titanium oxide coating, characterized in that a layer of hard material is provided between the main body and the titanium oxide coating on the main body.

17. Surgical instrument according to claim 16, characterized in that the layer of hard material has a thickness between 2 μm and 10 μm.

18. Surgical instrument according to claim 16, characterized in that the layer of hard material comprises titanium nitride and/or chromium nitride.

19. Surgical instrument according to claim 16, characterized in that between the main body and the layer of hard material, a bonding layer is provided.

20. Surgical instrument according to claim 16, characterized in that the layer of hard material is deposited as a gradient layer and thus a gradual transition to the titanium oxide layer is achieved.

21. Surgical instrument according to claim 16, characterized in that between the main body and the layer of hard material, a bonding layer of chromium is provided.

\* \* \* \* \*